United States Patent
Stierli et al.

(10) Patent No.: US 8,536,215 B2
(45) Date of Patent: Sep. 17, 2013

(54) PYRAZOLE MICROBIOCIDES

(75) Inventors: Daniel Stierli, Stein (CH); Harald Walter, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/579,848

(22) PCT Filed: Feb. 3, 2011

(86) PCT No.: PCT/EP2011/051538
§ 371 (c)(1),
(2), (4) Date: Aug. 17, 2012

(87) PCT Pub. No.: WO2011/101256
PCT Pub. Date: Aug. 25, 2011

(65) Prior Publication Data
US 2012/0329847 A1    Dec. 27, 2012

(30) Foreign Application Priority Data
Feb. 18, 2010    (EP) ..................... 10153924

(51) Int. Cl.
*A01N 43/56* (2006.01)
*C07D 231/12* (2006.01)
*C07D 231/14* (2006.01)

(52) U.S. Cl.
USPC ....................... 514/406; 548/374.1

(58) Field of Classification Search
None
See application file for complete search history.

(56) References Cited

U.S. PATENT DOCUMENTS
5,416,103 A * 5/1995 Eicken et al. ................. 514/355

FOREIGN PATENT DOCUMENTS
EP         0589313      3/1994
WO      2007/039615     4/2007
WO      2008/084073     7/2008

OTHER PUBLICATIONS
International Search Report, International Application No. PCT/EP2011/051538, completion date: Apr. 1, 2011.

* cited by examiner

*Primary Examiner* — Kamal Saeed
(74) *Attorney, Agent, or Firm* — R. Kody Jones

(57) ABSTRACT

Compounds of formula (I) wherein $R_1$ is $C_1$-$C_4$alkyl or $C_1$-$C_4$haloalkyl; $R_2$ is $C_1$-$C_4$alkyl; $R_3$ is hydrogen or halogen; $R_4$ is hydrogen, $C_1$-$C_4$alkyl or $C_1$-$C_4$haloalkyl; $R_5$ is hydrogen, halogen, $C_1$-$C_4$alkyl or $C_1$-$C_4$haloalkyl; $G_1$ is a cyclohexenyl group which is mono- or polysubstituted by substituents selected from the group consisting of $C_1$-$C_6$alkyl, $C_1$-$C_6$alkoxy, $C_3$-$C_6$cycloalkyl and phenyl; said cyclohexenyl group can form together with a $C_1$-$C_4$ alkylene group a bicyclic system which can be mono- or poly-substituted by substituents selected from the group consisting of $C_1$-$C_6$alkyl, $C_1$-$C_6$alkoxy, $C_3$-$C_6$cycloalkyl and phenyl; are suitable for use as microbiocides.

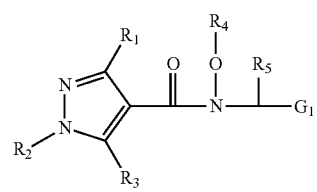

(I)

10 Claims, No Drawings

PYRAZOLE MICROBIOCIDES

This application is a 371 of International Application No. PCT/EP2011/051538 filed Feb. 3, 1011, which claims priority to EP 10153924.5 filed Feb. 18, 2010, the contents of which are incorporated herein by reference.

The present invention relates to novel microbiocidally active, in particular fungicidally active, carboxamides. It further relates to intermediates used in the preparation of these compounds, to compositions which comprise these compounds and to their use in agriculture or horticulture for controlling or preventing infestation of plants by phytopathogenic microorganisms, preferably fungi.

Fungicidally active carboxamides are for example described in WO 2007/039615. Herbicidally active carboxamides are described in WO 2008/084073.

It has been found that novel carboxamides have microbiocidal activity. The present invention accordingly relates to compounds of formula I

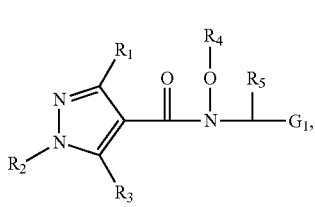

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl;
$G_1$ is a cyclohexenyl group which is mono- or polysubstituted by substituents selected from the group consisting of $C_1$-$C_6$alkyl, $C_1$-$C_6$alkoxy, $C_3$-$C_6$cycloalkyl and phenyl; said cyclohexenyl group can form together with a $C_1$-$C_4$alkylene group a bicyclic system which can be mono- or polysubstituted by substituents selected from the group consisting of $C_1$-$C_6$alkyl, $C_1$-$C_6$alkoxy, $C_3$-$C_6$cycloalkyl and phenyl; and agronomically acceptable salts/isomers/structural isomers/stereoisomers/diastereoisomers/enantiomers/tautomers and N-oxides of those compounds.

The invention covers all agronomically acceptable salts/isomers/structural isomers/stereoisomers/diastereoisomers/enantiomers/tautomers and N-oxides of those compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups—if present—can be mono- or di-unsaturated. The cycloalkyl groups occurring in the definitions of the substituents are, for example, cyclopropyl, cyclobutyl, cyclopentyl or cyclohexyl. Halogen is generally fluorine, chlorine, bromine or iodine, preferably fluorine, bromine or chlorine. This also applies, correspondingly, to halogen in combination with other meanings, such as haloalkyl or haloalkoxy. Haloalkyl groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Alkoxy is, for example, methoxy, ethoxy, propoxy, i-propoxy, n-butoxy, isobutoxy, sec-butoxy and tert-butoxy; preferably methoxy and ethoxy. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

In the context of the present invention "mono- or polysubstituted" in the definition of substituent $G_1$, means typically monosubstituted to seven-times substituted, preferably monosubstituted to five-times substituted, more preferably mono-, double- or triple-substituted.

The unsaturated bond of the cyclohexenyl group of substituent $G_1$ can be located at all chemically possible positions.

Examples for the meaning of $G_1$ as cyclohexenyl which can form together with a $C_1$-$C_4$alkylene group a bicyclic system are

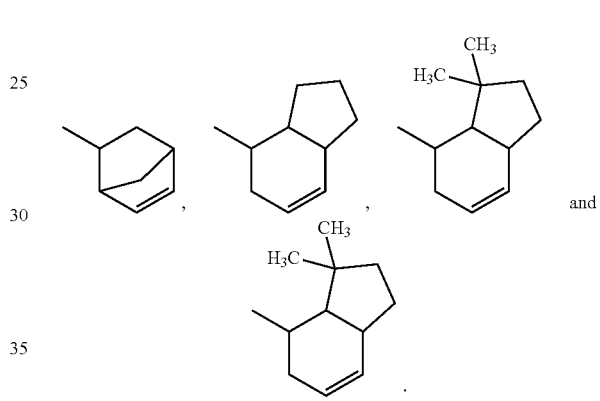

Preferred compounds of formula I are represented by the compounds of formula Ia

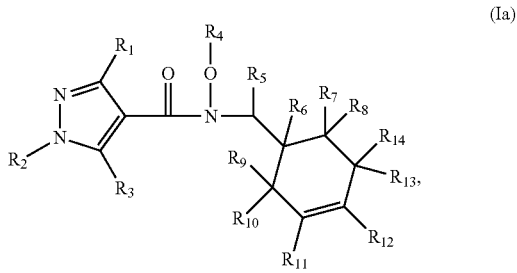

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl; and
$R_6$, $R_7$, $R_8$, $R_9$, $R_{10}$, $R_{11}$, $R_{12}$, $R_{13}$ and $R_{14}$, independently from each other, are hydrogen, $C_1$-$C_6$alkyl, $C_1$-$C_6$alkoxy, $C_3$-$C_6$cycloalkyl or phenyl; or $R_{10}$ and $R_{13}$ together or $R_9$ and $R_{14}$ together form a methylene or ethylene bridge which can be mono- or disubstituted by $C_1$-$C_4$alkyl.

Especially preferred are compounds of formula Ia as described above, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$ is hydrogen or $C_1$-$C_4$alkyl;
$R_6$ is hydrogen;
$R_7$ is hydrogen;
$R_8$ is hydrogen;
$R_9$ is hydrogen, $C_1$-$C_4$alkyl or $C_1$-$C_4$alkoxy,
$R_{10}$ is hydrogen or $C_1$-$C_4$alkyl;
$R_{11}$ is hydrogen or $C_1$-$C_4$alkyl;
$R_{12}$ is hydrogen or $C_1$-$C_4$alkyl;
$R_{13}$ is hydrogen or $C_1$-$C_4$alkyl;
$R_{14}$ is hydrogen;
or $R_{10}$ and $R_{13}$ together form a methylene or ethylene bridge which can be mono- or disubstituted by $C_1$-$C_4$alkyl.

Of particular interest are compounds of formula Ia as described above, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$ is $C_1$-$C_4$alkyl;
$R_6$, $R_7$ and $R_8$ are hydrogen;
$R_9$ is $C_1$-$C_4$alkyl;
$R_{10}$ is $C_1$-$C_4$alkyl;
$R_{11}$ is hydrogen;
$R_{12}$ is $C_1$-$C_4$alkyl;
$R_{13}$ and $R_{14}$ are hydrogen.

A further group of compounds of formula I which are especially preferred are represented by the compounds of formula Ie

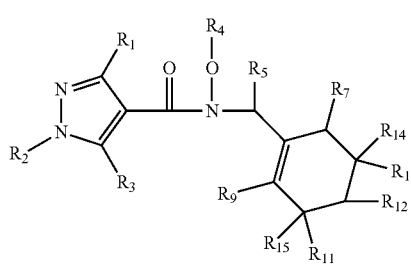

(Ie)

$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl;
$R_7$, $R_9$, $R_{11}$, $R_{12}$, $R_{13}$ and $R_{14}$ and $R_{15}$ independently from each other, are hydrogen, $C_1$-$C_6$alkyl, $C_1$-$C_6$alkoxy, $C_3$-$C_6$cycloalkyl or phenyl;
and $R_{12}$ is hydrogen or $C_1$-$C_4$alkyl; or $R_{11}$ and $R_{14}$ together or $R_{15}$ and $R_{13}$ together form a methylene or ethylene bridge which can be mono- or disubstituted by $C_1$-$C_4$alkyl.

Especially preferred are compounds of formula Ie as described above, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$, $R_7$, $R_9$, $R_{11}$, $R_{13}$ and $R_{14}$ and $R_{15}$ are hydrogen and $R_{12}$ is hydrogen or $C_1$-$C_4$alkyl.

In a preferred group of compounds of formula I, $R_4$ is methyl.

In further preferred compounds of formula I, $R_5$ is methyl.

Particularly preferred compounds of formula I are those, wherein $R_1$ is difluoromethyl, $R_2$ is methyl and $R_3$ is hydrogen.

Compounds of formula I may be prepared by reacting a compound of formula II

(II)

wherein $R_4$, $R_5$ and $G_1$ are as defined under formula I, with a compound of formula III

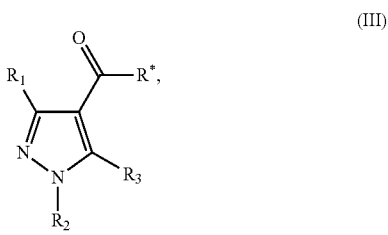

(III)

in which $R_1$, $R_2$ and $R_3$ are as defined under formula I, and R* is halogen, hydroxy or $C_{1-6}$ alkoxy, preferably chloro.

The reactions to give compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

When R* is hydroxy, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI), may be used.

The Intermediates of Formula II

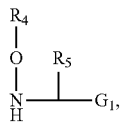
(II)

wherein the substituents are as defined under formula Ia, preferably wherein $R_4$ is $C_1$-$C_4$alkyl; are novel and were wherein $R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl;
$R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl;
$R_6$, $R_7$, $R_8$, $R_9$, $R_{10}$, $R_{11}$, $R_{12}$, $R_{13}$ and $R_{14}$, independently from each other, are hydrogen, $C_1$-$C_6$alkyl, $C_1$-$C_6$alkoxy, $C_3$-$C_6$cycloalkyl or phenyl; or $R_{10}$ and $R_{13}$ together or $R_9$ and $R_{14}$ together form a methylene or ethylene bridge which can be mono- or disubstituted by $C_1$-$C_4$alkyl; may be prepared as described in reaction scheme 1.

Scheme 1:

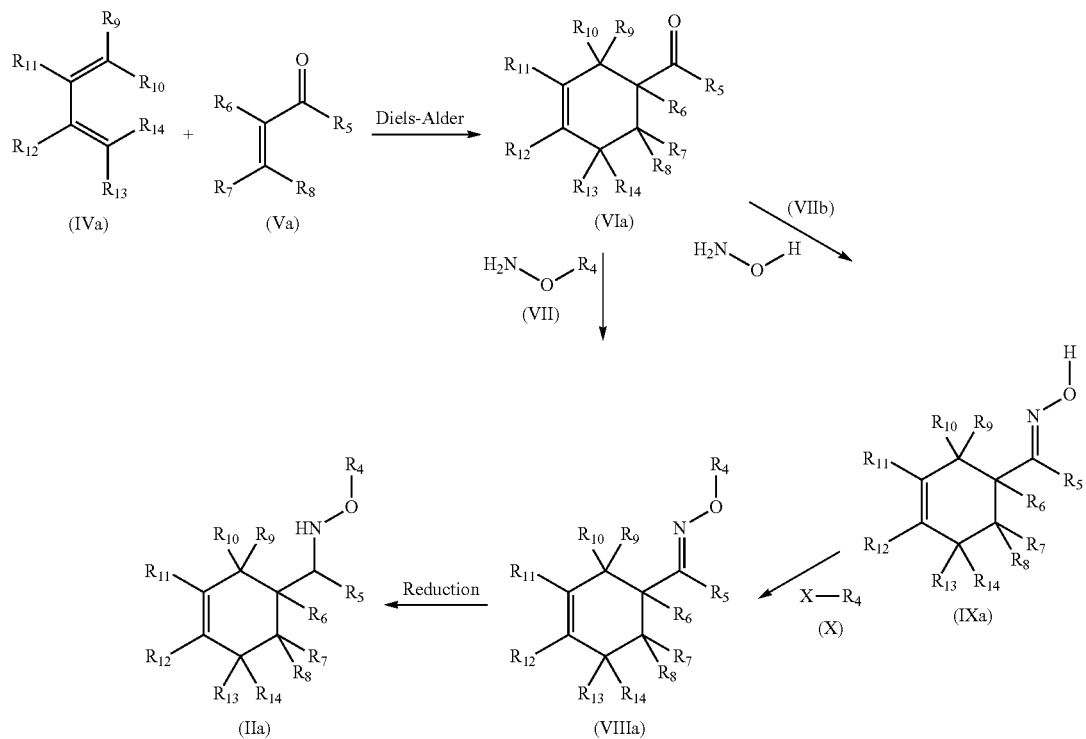

developed specifically for the preparation of the compounds of the formula I. Accordingly, these intermediates of formula II also form a part of the subject-matter of the present invention. The preferred substituent definitions for the compounds of formula I are also valid for the compound of formula II.

Intermediates of Formula IIa

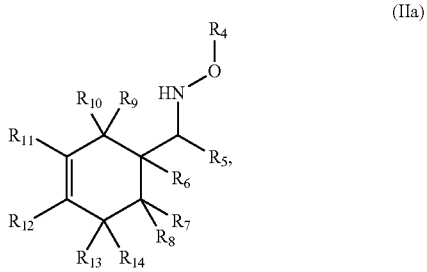
(IIa)

Ketones of formula VIa, in which $R_5$, $R_6$, $R_7$, $R_8$, $R_9$, $R_{10}$, $R_{11}$, $R_{12}$, $R_{13}$ and $R_{14}$ are as defined under formula IIa, can be prepared by the Diels-Alder cycloaddition of α,β-unsaturated ketones (Dienophile) of formula Va, in which $R_5$, $R_6$, $R_7$, and $R_8$ are as defined under formula IIa with a Diene of formula IVa, in which $R_9$, $R_{10}$, $R_{11}$, $R_{12}$, $R_{13}$ and $R_{14}$ are as defined under formula IIa, in the presence of a Al, B or Sn derivative Lewis acid as catalyst. The reaction may be performed in an organic solvent or under solvent free conditions at temperatures between ambient temperature and reflux temperature. Solvent free conditions are known from the literature: *Dienes in the Diels-Alder Reaction*; John Wiley & Sons: New York. The catalysts necessary for the Diels-Alder reaction are well known by a person skilled in the art, however on may cite, as non limiting examples, the following compounds: $AlCl_3$, $AlCl_3$*2THF, $SnCl_4$, $BF_3$, known from the literature: *Lewis Acids in Organic Synthesis*; Yamamoto, H., Ed.; Wiley-VCH.

Oxime ether derivatives of formula VIIIa, wherein the substituents are as defined under formula IIa, may be prepared by oximation of ketones of formula VIa with O-alkyl hydroxylamine derivatives of formula VII or a salt thereof. Suitable solvents carrying out the oximation step are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide, N-methylpyrrolidinone, alcohols such as methanol, ethanol, n-propanol, i-propanol, n-butanol, sec.butanol water or mixtures. The reaction temperatures are advantageously between −20° C. and +120° C. In general, the reactions can be carried out at ambient temperature. Suitable bases are, in particular pyridine, tertiary amines such as trimethylamine, triethylamine, huenig base, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases.

Alternatively, oxime ether derivatives of formula VIIIa may be prepared by O-alkylation of oxime derivatives of formula IXa with a compound of formula X, in which $R_4$ is $C_1$-$C_4$alkyl or $C_1$-$C_4$haloalkyl and X represents a leaving group, such as halogen, mesylate or tosylate, in the presence of a base. The alkylation reaction is advantageously carried out in aprotic inert organic solvents. Such solvents are hydrocarbons such as benzene, toluene, xylene or cyclohexane, ethers such as diethyl ether, ethylene glycol dimethyl ether, diethylene glycol dimethyl ether, tetrahydrofuran or dioxane, amides such as N,N-dimethylformamide, diethylformamide or N-methylpyrrolidinone. The reaction temperatures are between −20° C. and +120° C. Suitable bases are inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example crown ether, in particular 18-crown-6, or a tetraalkylammonium salt.

O-Alkylhydroxylamines of formula IIa may be prepared by the reduction of O-alkoxy oxime derivatives of formula VIIIa. It will be appreciated by those skilled in the art that this reduction can be carried out with a number of different reducing agents.

Compounds of formula II, wherein the unsaturated bond of the cyclohexene group of G is located at other positions as described in formula IIa, might be available by isomerisation of the compound of formula IIa.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention therefore also relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB (b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants (auxiliaries) can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection. According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATORY EXAMPLES

General Procedure for High Speed Synthesis

Example P0

Preparation of 3-difluoromethyl-1-methyl-1H-pyrazole-4-carboxylic acid methoxy-[-cyclohexenyl)-ethyl]-amide

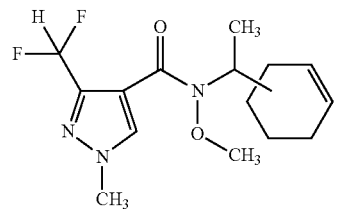

Step I:

To a stirred solution of a cyclohexenyl-ethanone (0.06 mmol), in acetic acid (500 µl) was added methoxyamine (4.7 mg). The reaction mixture was stirred at 24° C. for 48 h under nitrogen to obtain the cyclohexenyl-ethanone O-methyl-oxime.

Step II:

To the cyclohexenyl-ethanone O-methyl-oxime from step I, a suspension of sodium cyanoborohydride (11.3 mg) in DCE (200 µl) was added portionwise. The reaction mixture was stirred at 24° C. for 18 h under nitrogen. Most of acetic acid was removed under a stream of nitrogen to afford O-methyl-N-[cyclohexenyl)-ethyl]-hydroxylamine.

Step III:

To O-methyl-N-[cyclohexenyl)-ethyl]-hydroxylamine, prepared as described in step II, NaOH 0.75 molar (300 µl) and NaOH 2.0 molar (500 µl) were added. Followed by the addition of the addition of 3-difluoromethyl-1-methyl-1H-pyrazole-4-carbonyl chloride (11.7 mg) dissolved in dichloromethane (300 µl). The reaction mixture was stirred at ambient temperature for 18 hours under nitrogen atmosphere. The solvent was removed under a stream of nitrogen, followed by addition of acetic acid (200 µl), water (100 µl), DMA (200 µl) and acetonitrile (200 µl). The crude 3-difluoromethyl-1-methyl-1H-pyrazole-4-carboxylic acid methoxy-[-cyclohexenyl)-ethyl]-amides were directly submitted for LC Chromatography.

Purification:

The following purification method was used:

LC1 oder Z (Filename Z) Standard_Long gradient

Method B

| | |
|---|---|
| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
| LC | Alliance 2795 LC HPLC from Waters: quaternary pump, heated column compartment and diode-array detector. Column: Waters Atlantis dc18; length: 20 mm; internal |

-continued diameter: 3 mm; particle size: 3 μm, temperature (° C.) 40, DAD wavelength range (nm): 200 to 500, solvent gradient: A = 0.1% of formic acid in water and B: 0.1% of formic acid in acetonitrile.

| Time (min) | A % | B % | Flow (ml/min) |
|---|---|---|---|
| 0.0 | 80 | 20 | 1.7 |
| 5.0 | 0.0 | 100 | 1.7 |
| 5.6 | 0.0 | 100 | 1.7 |
| 6.0 | 80 | 20 | 1.7 |

Compounds prepared were analysed by method for LC-MS Method C described in Table 7:

Example P1

Preparation of 3-difluoromethyl-1-methyl-1H-pyrazole-4-carboxylic acid methoxy-[1-(2,2,4-trimethyl-cyclohex-3-enyl)-ethyl]-amide (compound 1.081)

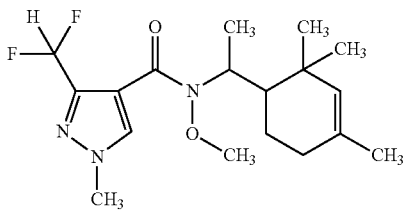 [SMILES: CON(C(=O)c1cn(C)nc1C(F)F)C(C)C1CCC(C)=CC1(C)C]

To a stirred solution of O-methyl-N-[1-(2,2,4-trimethyl-cyclohex-3-enyl)-ethyl]-hydroxylamine, prepared as described in example P6, (166 g; 0.84 mol) and triethylamine (140 ml; 1.01 mol) in dichloromethane (700 ml) under nitrogen atmosphere at a temperature of 15° C. was added dropwise 3-difluoromethyl-1-methyl-1H-pyrazole-4-carbonyl chloride (170 g; 0.84 mol) dissolved in dichloromethane (300 ml). The reaction mixture was stirred at 24° C. for 16 h under nitrogen atmosphere. The mixture was washed with a mixture of water (600 ml), brine (200 ml) and 1M hydrochloric acid (200 ml). The aqueous phase was extracted with dichloromethane (500 ml) and combined organic layers were dried over sodium sulfate. The solvent was removed in vacuo to afford 335 g of a sticky yellow oil which was subject to column chromatography (eluant: cyclohexane/ethyl acetate 90:10 to 70:30) to afford 203 g (68% of theory) of 3-difluoromethyl-1-methyl-1H-pyrazole-4-carboxylic acid methoxy-[1-(2,2,4-trimethyl-cyclohex-3-enyl)-ethyl]-amide (2 diastereomers) as a sticky light yellow solid (melting point: 95-105° C.).

Combination of Signals Corresponding to Both Diastereomers A & B:

Diastereomer A:
$^1$H NMR (400 MHz, CHCl3-d) δ ppm 0.92 (s, 3H), 1.10 (s, 3H), 1.31-2.00 (m, 5H), 1.48 (d, J=7.0 Hz, 3H), 1.62 (s, 3H), 3.71 (s, 3H), 3.98 (s, 3H), 4.53-4.73 (m, 1H), 4.90-5.04 (m, 1H), 7.27 (t, J=1.0 Hz, 1H), 7.88 (s, 1H).
MS [M+H]$^+$ 356/357.

Diastereomer B:
$^1$H NMR (400 MHz, CHCl3-d) δ ppm 0.87 (s, 3H), 1.02 (s, 3H), 1.22-2.08 (m, 5H), 1.32 (d, J=7.0 Hz, 3H), 1.61 (s, 3H), 3.71 (s, 3H), 3.97 (s, 3H), 4.69-4.88 (m, 1H), 5.01 (s, 1H), 7.25 (t, J=1.0 Hz, 1H), 7.86 (s, 1H).
MS [M+H]$^+$ 356/357.

Example P2

Preparation of 3-difluoromethyl-1-methyl-1H-pyrazole-4-carboxylic acid methoxy-[1-(2,2,4-trimethyl-cyclohex-3-enyl)-ethyl]-amide Diastereomer A (Compound 1.081 Diastereomer A)

To a stirred solution of O-methyl-N-[1-(2,2,4-trimethyl-cyclohex-3-enyl)-ethyl]-hydroxylamine (diastereomer A), prepared as described in example P7, (88 mg; 0.45 mmol) and triethylamine (75 μl; 0.54 mmol) in dichloromethane (2 ml) was added dropwise 3-difluoromethyl-1-methyl-1H-pyrazole-4-carbonyl chloride (87 mg; 0.45 mmol). The reaction mixture was stirred at 24° C. for 16 h under nitrogen atmosphere. The mixture was concentrated to an oil which was subject to flash-master column chromatography (elution gradient: cyclohexane/ethyl acetate 99:1 to 1:99) to afford 106 mg (66% of theory) of 3-difluoromethyl-1-methyl-1H-pyrazole-4-carboxylic acid methoxy-[1-(2,2,4-trimethyl-cyclohex-3-enyl)-ethyl]-amide as an amorph solid.

Diastereomer A: $^1$H NMR (400 MHz, CHCl3-d) δ ppm 0.92 (s, 3H), 1.10 (s, 3H), 1.31-2.00 (m, 5H), 1.48 (d, J=7.0 Hz, 3H), 1.62 (s, 3H), 3.71 (s, 3H), 3.98 (s, 3H), 4.53-4.73 (m, 1H), 4.90-5.04 (m, 1H), 7.27 (t, J=1.0 Hz, 1H), 7.88 (s, 1H).
MS [M+H]$^+$ 356/357.

Example P3

Preparation of 3-difluoromethyl-1-methyl-1H-pyrazole-4-carboxylic acid methoxy-[1-(2,2,4-trimethyl-cyclohex-3-enyl)-ethyl]-amide Diastereomer A (Compound 1.081 Diastereomer B)

To a stirred solution of O-methyl-N-[1-(2,2,4-trimethyl-cyclohex-3-enyl)-ethyl]-hydroxylamine (diastereomere B), prepared as described in example P7, (58 mg; 0.29 mmol) and triethylamine (50 μl; 0.35 mmol) in dichloromethane (1.2 ml) was added dropwise 3-difluoromethyl-1-methyl-1H-pyrazole-4-carbonyl chloride (57 mg; 0.29 mmol). The reaction mixture was stirred at 24° C. for 16 hours under nitrogen. The mixture was concentrated to an oil which was subject to flash-master column chromatography (Elution gradient: cyclohexane/ethyl acetate 99:1 to 1:99) to afford 80 mg (78% of theory) of 3-difluoromethyl-1-methyl-1H-pyrazole-4-carboxylic acid methoxy-[1-(2,2,4-trimethyl-cyclohex-3-enyl)-ethyl]-amide as a clear oil.

Diastereomer B: $^1$H NMR (400 MHz, CHCl$_3$-d) δ ppm 0.87 (s, 3H), 1.02 (s, 3H), 1.22-2.08 (m, 5H), 1.32 (d, J=7.0 Hz, 3H), 1.61 (s, 3H), 3.71 (s, 3H), 3.97 (s, 3H), 4.69-4.88 (m, 1H), 5.01 (s, 1H), 7.25 (t, J=1.0 Hz, 1H), 7.86 (s, 1H).
MS [M+H]$^+$ 356/357.

Example P4

Preparation of 1-(2,2,4-trimethyl-cyclohex-3-enyl)-ethanone)

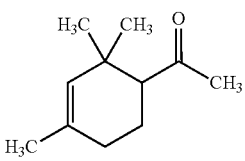

In a 500 ml sulfonation flask with cooling funnel, dropping funnel and mechanical stirring under air (*) at 5° C. was added but-3-en-2-one (43 ml; 0.52 mol) then THF (4.2 ml; 52 mmol) followed by a careful portionwise addition of aluminum chloride (3.5 g; 26 mmol). White fumes and increase of temperature to 20° C. were observed. The mixture turned red. The temperature was decreased to 15° C. and 2,4-dimethyl-1,3-pentadiene (68 ml; 0.52 mol) was added dropwise (90 min). Exothermic reaction was observed. The reaction mixture was stirred for 8 hours at 25° C. and for 10 hours at 45° C. As the diene was still detected but-3-en-2-one was added dropwise (22 ml; 0.26 mol) (10 min) and the mixture was stirred for additional 48 hours at 25° C. Dichloromethane (200 ml) was added to the mixture which was stirred for 5 min and filtered over celite. The red solution obtained was poured into cold water (1 l) and extracted with dichloromethane (4×300 ml). Combined organic layers were washed with brine (500 ml) and water (500 ml), dried over sodium sulfate and filtered over silica. The solvent was removed in vacuo to afford 84 g (97% of theory) of 1-(2,2,4-trimethyl-cyclohex-3-enyl)-ethanone as a clear red oil.

$^1$H NMR (400 MHz, CHCl$_3$-d) δ ppm 0.92 (s, 3H), 1.11 (s, 3H), 1.63 (d, J=1.0 Hz, 3H), 1.66-2.16 (m, 4H), 2.18 (s, 3H), 2.42-2.48 (m, 1H), 5.01-5.08 (m, 1H).

GC/MS: retention time 6.16; [M]+ 166 (see method at the bottom).

REFERENCE

*Organic Letters*, 2006, *Vol.* 8, *No.* 12, 2487-2489
*[AlCl3+2THF]: A New and Efficient Catalytic System for Diels-Alder Cycloaddition of α,β-Unsaturated Carbonyl Compounds under Solvent-Free Conditions*

Example P5

Preparation of
1-(2,2,4-trimethyl-cyclohex-3-enyl)-ethanone
O-methyl-oxime

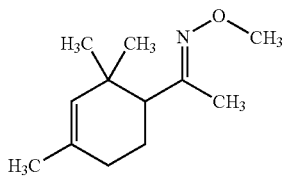

To a stirred solution of 1-(2,2,4-trimethyl-cyclohex-3-enyl)-ethanone (162 g; 0.97 mol), prepared as described in example P4, in methanol (500 ml) was added pyridine (160 ml; 1.95 mol) followed by a portionwise addition of methoxyamine hydrochloride (142 g; 1.70 mol). The reaction mixture was stirred at 24° C. for 16 hours under nitrogen atmosphere. Methanol was removed under reduced pressure, the residue poured in water (600 ml) and 1N hydrochloric acid was added (100 ml). The solution was extracted with dichloromethane (3×300 ml). Combined organic layers were washed with brine (500 ml) and dried over sodium sulfate. The solvent was removed in vacuo to afford 175 g (92% of theory) of 1-(2,2,4-trimethyl-cyclohex-3-enyl)-ethanone O-methyl-oxime as a clear red oil.
Major Isomere:

$^1$H NMR (400 MHz, CHC$_3$-d) δ ppm 0.88 (s, 3H), 1.01 (s, 3H), 1.51-2.01 (m, 4H), 1.63 (s, 3H), 1.80 (s, 3H), 2.24 (dd, J=12.3, 2.8 Hz, 1H), 3.85 (s, 3H), 5.06-5.11 (m, 1H).

MS [M+H]$^+$ 196/197.

GC/MS: retention time 6.69; [M]$^+$ 195 (see method at the bottom)

Example P6

Preparation of O-methyl-N-[1-(2,2,4-trimethyl-cyclohex-3-enyl)-ethyl]-hydroxylamine

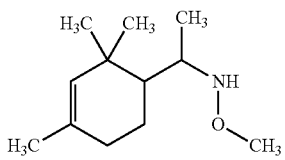

To a stirred solution of 1-(2,2,4-trimethyl-cyclohex-3-enyl)-ethanone O-methyl-oxime (135 g; 0.69 mol), prepared as described in example P5, in acetic acid (650 ml) was added portionwise sodium cyanoborohydride (67 g; 1.04 mol). The reaction mixture was stirred at 24° C. for 16 hours under nitrogen atmosphere. Most of acetic acid was removed under reduced pressure. The yellow sticky oil obtained was poured in 2M sodium hydroxide (800 ml) and water (100 ml). The solution was extracted with dichloromethane (3×300 ml). Combined organic layers were washed with sodium bicarbonate (500 ml) and dried over sodium sulfate. The solvent was removed in vacuo to afford 128 g (94% of theory) of O-methyl-N-[1-(2,2,4-trimethyl-cyclohex-3-enyl)-ethyl]-hydroxylamine (mixture of two diastereomers) as a cloudy yellow oil.

Combination of Signals Corresponding to the Two Diastereomers A & B:

Diastereomer A: $^1$H NMR (400 MHz, CHCl$_3$-d) δ ppm 0.98 (s, 3H), 1.00 (s, 3H), 1.18 (d, J=6.2 Hz, 3H), 1.21-2.01 (m, 5H), 3.22-3.43 (m, 1H), 3.50 (s, 3H), 4.97-5.06 (m, 1H), 5.40-5.58 (m, 1H).

MS [M+H]$^+$ 198/199.

Diastereomer B: $^1$H NMR (400 MHz, CHCl$_3$-d) δ ppm 0.86 (s, 3H), 0.98 (d, J=6.6 Hz, 3H), 1.02 (s, 3H), 1.23-1.99 (m, 5H), 3.29 (q, J=6.5 Hz, 1H), 3.53 (s, 3H), 4.99-5.05 (m, 1H), 5.20-5.37 (m, 1H).

MS [M+H]$^+$ 198/199.

Example P7

Preparation of O-methyl-N-[1-(2,2,4-trimethyl-cyclohex-3-enyl)-ethyl]-hydroxylamine—Separation of Both Diastereomers

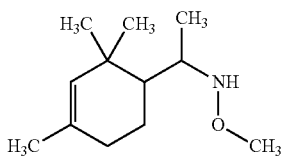

syn separated from anti

To a stirred solution of 1-(2,2,4-trimethyl-cyclohex-3-enyl)-ethanone O-methyl-oxime (0.27 g; 1.40 mmol) in acetic acid (3 mL) was added portionwise sodium cyanoborohydride (0.20 g; 3.00 mmol). The reaction mixture was stirred at 24° C. for 16 hours under nitrogen atmosphere. Most of acetic acid was removed under reduced pressure. The yellow sticky oil obtained was dissolved in dichloromethane and poured in 1M sodium hydroxide which was extracted with dichloromethane. Combined organic layers were washed with sodium bicarbonate and dried over sodium sulfate. The solvent was removed in vacuo to afford 0.26 g of colorless oil which was subject to flash-master column chromatography (Elution gradient: cyclohexane/ethyl acetate 99:1 to 80:20) to afford 88 mg (33% of theory) of diastereomer A as a clear oil and 58 mg (22% of theory) of diastereomer B as a clear oil.

Diastereomer A:

$^1$H NMR (400 MHz, CHLOROFORM-d) δ ppm 0.98 (s, 3H), 1.00 (s, 3H), 1.18 (d, J=6.2 Hz, 3H), 1.21-2.01 (m, 5H), 3.22-3.43 (m, 1H), 3.50 (s, 3H), 4.97-5.06 (m, 1H), 5.40-5.58 (m, 1H).

MS [M+H]$^+$ 198/199.

Diastereomer B:

$^1$H NMR (400 MHz, CHLOROFORM-d) δ ppm 0.86 (s, 3H), 0.98 (d, J=6.6 Hz, 3H), 1.02 (s, 3H), 1.23-1.99 (m, 5H), 3.29 (q, J=6.5 Hz, 1H), 3.53 (s, 3H), 4.99-5.05 (m, 1H), 5.20-5.37 (m, 1H).

MS [M+H]$^+$ 198/199.

Tables 1 to 3: Compounds of Formula Ib:

The invention was further illustrated by the preferred individual compounds of formula (Ib) listed below in Tables 1 to 3. Characterising data is given in Table 10.

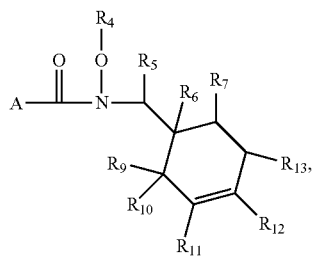

(Ib)

In the compounds of formula Ib, A is selected from the groups consisting of $A_1$

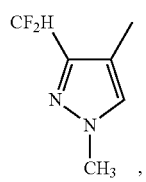

(A$_1$)

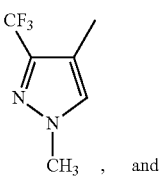

(A$_2$)

and

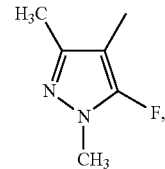

(A$_3$)

Each of Tables 1 to 3, which follow the Table Y below, comprises 110 compounds of formula (Ib) in which $R_4$, $R_5$, $R_6$, $R_7$, $R_9$, $R_{10}$, $R_{11}$, $R_{12}$ and $R_{13}$ have the values given in Table Y and A has the value given in the relevant Table 1 to 3. Thus Table 1 corresponds to Table Y when Y is 1 and A has the value given under the Table 1 heading, Table 2 corresponds to Table Y when Y is 2 and A has the value given under the Table 2 heading, and so on for Tables 3.

TABLE Y ("Me" ist the methyl group, "Et" is the ethyl group, "c-Pr" means cyclopropyl):

| Cpd No. | $R_4$ | $R_5$ | $R_6$ | $R_7$ | $R_9$ | $R_{10}$ | $R_{11}$ | $R_{12}$ | $R_{13}$ |
|---|---|---|---|---|---|---|---|---|---|
| Y.001 | Me | H | H | H | H | H | H | H | H |
| Y.002 | Me | H | H | H | H | H | H | Me | H |
| Y.003 | Me | H | H | H | H | H | H | Et | H |
| Y.004 | Me | H | H | H | H | H | H | n-Pr | H |
| Y.005 | Me | H | H | H | H | H | H | c-Pr | H |
| Y.006 | Me | H | H | H | H | H | H | n-Bu | H |
| Y.007 | Me | H | H | H | H | H | H | i-Bu | H |
| Y.008 | Me | H | H | H | H | H | H | Ph | H |
| Y.009 | Me | H | H | H | Me | H | H | H | H |
| Y.010 | Me | H | H | H | Et | H | H | H | H |
| Y.011 | Me | H | H | H | n-Pr | H | H | H | H |
| Y.012 | Me | H | H | H | c-Pr | H | H | H | H |
| Y.013 | Me | H | H | H | n-Bu | H | H | H | H |
| Y.014 | Me | H | H | H | Ph | H | H | H | H |
| Y.015 | Me | H | H | H | OMe | H | H | H | H |
| Y.016 | Me | H | H | H | Me | H | H | Me | H |
| Y.017 | Me | H | H | H | Me | H | H | Et | H |
| Y.018 | Me | H | H | H | Me | H | H | n-Pr | H |
| Y.019 | Me | H | H | H | Me | H | H | c-Pr | H |
| Y.020 | Me | H | H | H | Me | H | H | Ph | H |
| Y.021 | Me | H | H | H | Et | H | H | Me | H |
| Y.022 | Me | H | H | H | Et | H | H | Et | H |
| Y.023 | Me | H | H | H | Et | H | H | n-Pr | H |
| Y.024 | Me | H | H | H | Et | H | H | c-Pr | H |
| Y.025 | Me | H | H | H | Et | H | H | Ph | H |
| Y.026 | Me | H | H | H | OMe | H | H | Me | H |
| Y.027 | Me | H | H | H | OMe | H | H | Et | H |
| Y.028 | Me | H | H | H | OMe | H | H | n-Pr | H |
| Y.029 | Me | H | H | H | OMe | H | H | c-Pr | H |
| Y.030 | Me | H | H | H | OMe | H | H | Ph | H |
| Y.031 | Me | H | H | H | Me | Me | H | H | H |
| Y.032 | Me | H | H | H | Me | Et | H | H | H |
| Y.033 | Me | H | H | H | Et | Et | H | H | H |
| Y.034 | Me | H | H | H | Me | Me | H | Me | H |
| Y.035 | Me | H | H | H | Me | Et | H | Me | H |
| Y.036 | Me | H | H | H | Et | Et | H | Me | H |
| Y.037 | Me | H | H | H | Me | Me | H | Me | H |
| Y.038 | Me | H | H | H | Me | Me | H | Et | H |
| Y.039 | Me | H | H | H | Me | Me | H | c-Pr | H |
| Y.040 | Me | H | H | H | H | H | Me | Me | H |
| Y.041 | Me | H | H | H | H | H | Et | Et | H |
| Y.042 | Me | H | H | H | H | H | (CH$_2$)$_2$ | | H |
| Y.043 | Me | H | H | H | H | H | (CH$_2$)$_3$ | | H |
| Y.044 | Me | H | H | H | H | H | (CH$_2$)$_4$ | | H |
| Y.045 | Me | H | H | H | Me | H | Me | Me | H |
| Y.046 | Me | H | H | H | H | (CH$_2$) connected to R$_{13}$ | H | H | |

TABLE Y-continued ("Me" ist the methyl group, "Et" is the ethyl group, "c-Pr" means cyclopropyl):

| Cpd No. | $R_4$ | $R_5$ | $R_6$ | $R_7$ | $R_9$ | $R_{10}$ | $R_{11}$ | $R_{12}$ | $R_{13}$ |
|---|---|---|---|---|---|---|---|---|---|
| Y.047 | Me | H | H | H | H | $(CH_2)_2$ connected to $R_{13}$ | H | H | |
| Y.048 | Me | Me | H | H | H | H | H | H | H |
| Y.049 | Me | Me | H | H | H | H | H | Me | H |
| Y.050 | Me | Me | H | H | H | H | H | Et | H |
| Y.051 | Me | Me | H | H | H | H | H | n-Pr | H |
| Y.052 | Me | Me | H | H | H | H | H | c-Pr | H |
| Y.053 | Me | Me | H | H | H | H | H | n-Bu | H |
| Y.054 | Me | Me | H | H | H | H | H | i-Bu | H |
| Y.055 | Me | Me | H | H | H | H | H | Ph | H |
| Y.056 | Me | Me | H | H | Me | H | H | H | H |
| Y.057 | Me | Me | H | H | Et | H | H | H | H |
| Y.058 | Me | Me | H | H | n-Pr | H | H | H | H |
| Y.059 | Me | Me | H | H | c-Pr | H | H | H | H |
| Y.060 | Me | Me | H | H | n-Bu | H | H | H | H |
| Y.061 | Me | Me | H | H | Ph | H | H | H | H |
| Y.062 | Me | Me | H | H | OMe | H | H | H | H |
| Y.063 | Me | Me | H | H | Me | H | H | Me | H |
| Y.064 | Me | Me | H | H | Me | H | H | Et | H |
| Y.065 | Me | Me | H | H | Me | H | H | n-Pr | H |
| Y.066 | Me | Me | H | H | Me | H | H | c-Pr | H |
| Y.067 | Me | Me | H | H | Me | H | H | Ph | H |
| Y.068 | Me | Me | H | H | Et | H | H | Me | H |
| Y.069 | Me | Me | H | H | Et | H | H | Et | H |
| Y.070 | Me | Me | H | H | Et | H | H | n-Pr | H |
| Y.071 | Me | Me | H | H | Et | H | H | c-Pr | H |
| Y.072 | Me | Me | H | H | Et | H | H | Ph | H |
| Y.073 | Me | Me | H | H | OMe | H | H | Me | H |
| Y.074 | Me | Me | H | H | OMe | H | H | Et | H |
| Y.075 | Me | Me | H | H | OMe | H | H | n-Pr | H |
| Y.076 | Me | Me | H | H | OMe | H | H | c-Pr | H |
| Y.077 | Me | Me | H | H | OMe | H | H | Ph | H |
| Y.078 | Me | Me | H | H | Me | Me | H | H | H |
| Y.079 | Me | Me | H | H | Me | Et | H | H | H |
| Y.080 | Me | Me | H | H | Et | Et | H | H | H |
| Y.081 | Me | Me | H | H | Me | Me | H | Me | H |
| Y.082 | Me | Me | H | H | Me | Et | H | Me | H |
| Y.083 | Me | Me | H | H | Et | Et | H | Me | H |
| Y.084 | Me | Me | H | H | Me | Me | H | Me | H |
| Y.085 | Me | Me | H | H | Me | Me | H | Et | H |
| Y.086 | Me | Me | H | H | Me | Me | H | c-Pr | H |
| Y.087 | Me | Me | H | H | H | H | Me | Me | H |
| Y.088 | Me | Me | H | H | H | H | Et | Et | H |
| Y.089 | Me | Me | H | H | H | H | $(CH_2)_2$ | | H |
| Y.090 | Me | Me | H | H | H | H | $(CH_2)_3$ | | H |
| Y.091 | Me | Me | H | H | H | H | $(CH_2)_4$ | | H |
| Y.092 | Me | Me | H | H | Me | H | Me | Me | H |
| Y.093 | Me | Me | H | H | H | $(CH_2)$ connected to $R_{13}$ | H | H | |
| Y.094 | Me | Me | H | H | OMe | $(CH_2)_2$ connected to $R_{13}$ | H | H | |
| Y.095 | Me | Me | H | H | H | H | Me | H | Me |
| Y.096 | Me | Me | H | H | H | $(CH_2)CH(CH_3)C(CH_3)_2$ | | H | H |
| Y.097 | Me | H | Me | H | H | H | H | Me | H |
| Y.098 | Me | H | Me | H | Me | H | H | H | H |
| Y.099 | Me | H | Me | H | Et | H | H | H | H |
| Y.100 | Me | H | Me | H | Me | Me | H | Me | H |
| Y.101 | Me | Me | Me | H | H | H | H | H | H |
| Y.102 | Me | Me | Me | H | H | H | H | Me | H |
| Y.103 | Me | Me | Me | H | Me | H | H | H | H |
| Y.104 | Me | Me | Me | H | Et | H | H | H | H |
| Y.105 | Me | Me | Me | H | Me | Me | H | Me | H |
| Y.106 | Me | Me | H | Me | H | H | H | H | H |
| Y.107 | Me | Me | H | Me | H | H | H | Me | H |
| Y.108 | Me | Me | H | Me | Me | H | H | H | H |
| Y.109 | Me | Me | H | Me | Me | Et | H | H | H |
| Y.110 | Me | Me | H | Me | Me | Me | H | Me | H |

Table 1 provides 110 compounds of formula (Ib), wherein A is $A_1$.

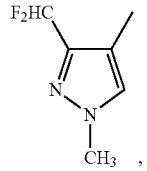

and $R_4$, $R_5$, $R_6$, $R_7$, $R_9$, $R_{10}$, $R_{11}$, $R_{12}$ and $R_{13}$ are as defined in Table Y.

For example, compound 1.049 has the following structure:

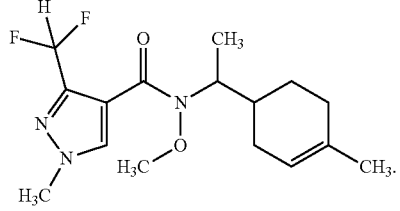

Table 2 provides 110 compounds of formula (Ib), wherein A is $A_2$.

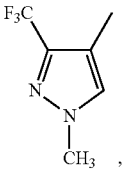

and $R_4$, $R_5$, $R_6$, $R_7$, $R_9$, $R_{10}$, $R_{11}$, $R_{12}$ and $R_{13}$ are as defined in Table Y.

For example, compound 2.001 has the following structure:

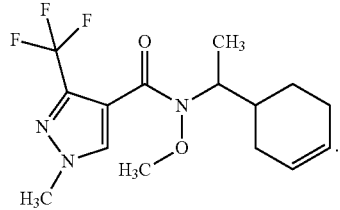

Table 3 provides 110 compounds of formula (Ib), wherein A is $A_3$.

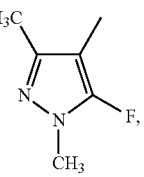

and $R_4$, $R_5$, $R_6$, $R_7$, $R_9$, $R_{10}$, $R_{11}$, $R_{12}$ and $R_{13}$ are as defined in Table Y.

For example, compound 3.081 has the following structure:

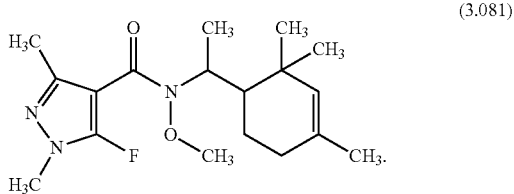 [SMILES: CON(C(=O)c1c(C)nn(C)c1F)C(C)C1CCC(C)=CC1(C)C]
(3.081)

Tables 4 to 6: Compounds of Formula Ic:

The invention is further illustrated by the preferred individual compounds of formula (Ic) listed below in Tables 4 to 6. Characterising data is given in Table 10.

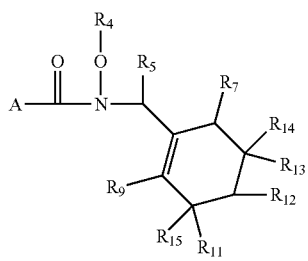
(Ic)

In the compounds of formula Ic, A is selected from the groups consisting of $A_1$

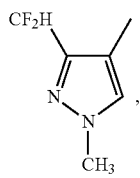
($A_1$)

$A_2$

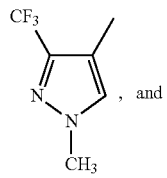
($A_2$)

$A_3$

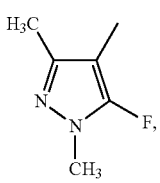
($A_3$)

Each of Tables 4 to 6, which follow the Table W below, comprises 110 compounds of formula (Ic) in which $R_4$, $R_5$, $R_7$, $R_9$, $R_{11}$, $R_{12}$, $R_{13}$, $R_{14}$ and $R_{15}$ have the values given in Table W and A has the value given in the relevant Table 4 to 6. Thus Table 4 corresponds to Table W when W is 4 and A has the value given under the Table 4 heading, Table 5 corresponds to Table W when W is 5 and A has the value given under the Table 5 heading, and so on for Tables 6.

TABLE W ("Me" ist the methyl group, "Et" is the ethyl group, "c-Pr" means cyclopropyl):

| Cpd No. | $R_4$ | $R_5$ | $R_9$ | $R_7$ | $R_{14}$ | $R_{13}$ | $R_{12}$ | $R_{15}$ | $R_{11}$ |
|---|---|---|---|---|---|---|---|---|---|
| W.001 | Me | H | H | H | H | H | H | H | H |
| W.002 | Me | H | H | H | H | H | H | Me | H |
| W.003 | Me | H | H | H | H | H | H | Et | H |
| W.004 | Me | H | H | H | H | H | H | n-Pr | H |
| W.005 | Me | H | H | H | H | H | H | c-Pr | H |
| W.006 | Me | H | H | H | H | H | H | n-Bu | H |
| W.007 | Me | H | H | H | H | H | H | i-Bu | H |
| W.008 | Me | H | H | H | H | H | H | Ph | H |
| W.009 | Me | H | H | H | Me | H | H | H | H |
| W.010 | Me | H | H | H | Et | H | H | H | H |
| W.011 | Me | H | H | H | n-Pr | H | H | H | H |
| W.012 | Me | H | H | H | c-Pr | H | H | H | H |
| W.013 | Me | H | H | H | n-Bu | H | H | H | H |
| W.014 | Me | H | H | H | Ph | H | H | H | H |
| W.015 | Me | H | H | H | OMe | H | H | H | H |
| W.016 | Me | H | H | H | Me | H | H | Me | H |
| W.017 | Me | H | H | H | Me | H | H | Et | H |
| W.018 | Me | H | H | H | Me | H | H | n-Pr | H |
| W.019 | Me | H | H | H | Me | H | H | c-Pr | H |
| W.020 | Me | H | H | H | Me | H | H | Ph | H |
| W.021 | Me | H | H | H | Et | H | H | Me | H |
| W.022 | Me | H | H | H | Et | H | H | Et | H |
| W.023 | Me | H | H | H | Et | H | H | n-Pr | H |
| W.024 | Me | H | H | H | Et | H | H | c-Pr | H |
| W.025 | Me | H | H | H | Et | H | H | Ph | H |
| W.026 | Me | H | H | H | OMe | H | H | Me | H |
| W.027 | Me | H | H | H | OMe | H | H | Et | H |
| W.028 | Me | H | H | H | OMe | H | H | n-Pr | H |
| W.029 | Me | H | H | H | OMe | H | H | c-Pr | H |
| W.030 | Me | H | H | H | OMe | H | H | Ph | H |
| W.031 | Me | H | H | H | Me | Me | H | H | H |
| W.032 | Me | H | H | H | Me | Et | H | H | H |
| W.033 | Me | H | H | H | Et | Et | H | H | H |
| W.034 | Me | H | H | H | Me | Me | H | Me | H |
| W.035 | Me | H | H | H | Me | Et | H | Me | H |
| W.036 | Me | H | H | H | Et | Et | H | Me | H |
| W.037 | Me | H | H | H | Me | Me | H | Me | H |
| W.038 | Me | H | H | H | Me | Me | H | Et | H |
| W.039 | Me | H | H | H | Me | Me | H | c-Pr | H |
| W.040 | Me | H | H | H | H | H | Me | Me | H |
| W.041 | Me | H | H | H | H | H | Et | Et | H |
| W.042 | Me | H | H | H | H | H | $(CH_2)_2$ | | H |
| W.043 | Me | H | H | H | H | H | $(CH_2)_3$ | | H |
| W.044 | Me | H | H | H | H | H | $(CH_2)_4$ | | H |
| W.045 | Me | H | H | H | Me | H | Me | Me | H |
| W.046 | Me | H | H | H | H | $(CH_2)$ connected to $R_{11}$ | H | H | |
| W.047 | Me | H | H | H | H | $(CH_2)_2$ connected to $R_{11}$ | H | H | |
| W.048 | Me | Me | H | H | H | H | H | H | H |
| W.049 | Me | Me | H | H | H | H | H | Me | H |
| W.050 | Me | Me | H | H | H | H | H | Et | H |
| W.051 | Me | Me | H | H | H | H | H | n-Pr | H |
| W.052 | Me | Me | H | H | H | H | H | c-Pr | H |
| W.053 | Me | Me | H | H | H | H | H | n-Bu | H |
| W.054 | Me | Me | H | H | H | H | H | i-Bu | H |
| W.055 | Me | Me | H | H | H | H | H | Ph | H |
| W.056 | Me | Me | H | H | Me | H | H | H | H |
| W.057 | Me | Me | H | H | Et | H | H | H | H |
| W.058 | Me | Me | H | H | n-Pr | H | H | H | H |
| W.059 | Me | Me | H | H | c-Pr | H | H | H | H |
| W.060 | Me | Me | H | H | n-Bu | H | H | H | H |
| W.061 | Me | Me | H | H | Ph | H | H | H | H |
| W.062 | Me | Me | H | H | OMe | H | H | H | H |
| W.063 | Me | Me | H | H | Me | H | H | Me | H |
| W.064 | Me | Me | H | H | Me | H | H | Et | H |
| W.065 | Me | Me | H | H | Me | H | H | n-Pr | H |
| W.066 | Me | Me | H | H | Me | H | H | c-Pr | H |

TABLE W-continued ("Me" ist the methyl group, "Et" is the ethyl group, "c-Pr" means cyclopropyl):

| Cpd No. | $R_4$ | $R_5$ | $R_9$ | $R_7$ | $R_{14}$ | $R_{13}$ | $R_{12}$ | $R_{15}$ | $R_{11}$ |
|---|---|---|---|---|---|---|---|---|---|
| W.067 | Me | Me | H | H | Me | H | H | Ph | H |
| W.068 | Me | Me | H | H | Et | H | H | Me | H |
| W.069 | Me | Me | H | H | Et | H | H | Et | H |
| W.070 | Me | Me | H | H | Et | H | H | n-Pr | H |
| W.071 | Me | Me | H | H | Et | H | H | c-Pr | H |
| W.072 | Me | Me | H | H | Et | H | H | Ph | H |
| W.073 | Me | Me | H | H | OMe | H | H | Me | H |
| W.074 | Me | Me | H | H | OMe | H | H | Et | H |
| W.075 | Me | Me | H | H | OMe | H | H | n-Pr | H |
| W.076 | Me | Me | H | H | OMe | H | H | c-Pr | H |
| W.077 | Me | Me | H | H | OMe | H | H | Ph | H |
| W.078 | Me | Me | H | H | Me | Me | H | H | H |
| W.079 | Me | Me | H | H | Me | Et | H | H | H |
| W.080 | Me | Me | H | H | Et | Et | H | H | H |
| W.081 | Me | Me | H | H | Me | Me | H | Me | H |
| W.082 | Me | Me | H | H | Me | Et | H | Me | H |
| W.083 | Me | Me | H | H | Et | Et | H | Me | H |
| W.084 | Me | Me | H | H | Me | Me | H | Me | H |
| W.085 | Me | Me | H | H | Me | Me | H | Et | H |
| W.086 | Me | Me | H | H | Me | Me | H | c-Pr | H |
| W.087 | Me | Me | H | H | H | H | Me | Me | H |
| W.088 | Me | Me | H | H | H | H | Et | Et | H |
| W.089 | Me | Me | H | H | H | H | $(CH_2)_2$ | | H |
| W.090 | Me | Me | H | H | H | H | $(CH_2)_3$ | | H |
| W.091 | Me | Me | H | H | H | H | $(CH_2)_4$ | | H |
| W.092 | Me | Me | H | H | Me | H | Me | Me | H |
| W.093 | Me | Me | H | H | H | $(CH_2)$ connected to $R_{11}$ | H | H | |
| W.094 | Me | Me | H | H | OMe | $(CH_2)_2$ connected to $R_{11}$ | H | H | |
| W.095 | Me | Me | H | H | H | H | Me | H | Me |
| W.096 | Me | Me | H | H | H | $(CH_2)CH(CH_3)C(CH_3)_2$ | | H | H |
| W.097 | Me | H | Me | H | H | H | H | Me | H |
| W.098 | Me | H | Me | H | Me | H | H | H | H |
| W.099 | Me | H | Me | H | Et | H | H | H | H |
| W.100 | Me | H | Me | H | Me | Me | H | Me | H |
| W.101 | Me | Me | Me | H | H | H | H | H | H |
| W.102 | Me | Me | Me | H | H | H | H | Me | H |
| W.103 | Me | Me | Me | H | Me | H | H | H | H |
| W.104 | Me | Me | Me | H | Et | H | H | H | H |
| W.105 | Me | Me | Me | H | Me | Me | H | Me | H |
| W.106 | Me | Me | H | Me | H | H | H | H | H |
| W.107 | Me | Me | H | Me | H | H | H | Me | H |
| W.108 | Me | Me | H | Me | Me | H | H | H | H |
| W.109 | Me | Me | H | Me | Et | H | H | H | H |
| W.110 | Me | Me | H | Me | Me | Me | H | Me | H |

Table 4 provides 110 compounds of formula (Ic), wherein A is $A_1$

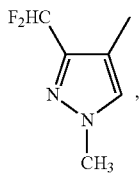

and $R_4$, $R_5$, $R_7$, $R_9$, $R_{11}$, $R_{12}$, $R_{13}$, $R_{14}$ and $R_{15}$ are as defined in Table W.

Table 5 provides 110 compounds of formula (Ic), wherein A is $A_2$

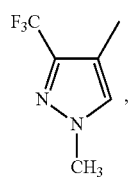

and $R_4$, $R_5$, $R_7$, $R_9$, $R_{11}$, $R_{12}$, $R_{13}$, $R_{14}$ and $R_{15}$ are as defined in Table W.

Table 6 provides 110 compounds of formula (Ic), wherein A is $A_3$

and $R_4$, $R_5$, $R_7$, $R_9$, $R_{11}$, $R_{12}$, $R_{13}$, $R_{14}$ and $R_{15}$ are as defined in Table W.

Tables 7 to 9: Compounds of Formula Ic:

The invention is further illustrated by the preferred individual compounds of formula (Id) listed below in Tables 7 to 9. Characterising data is given in Table 10.

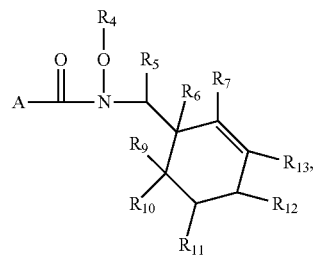

In the compounds of formula Id, A is selected from the groups consisting of $A_1$

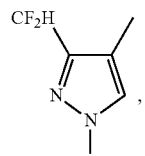

$A_2$

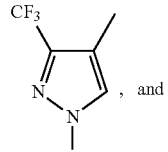

, and

A$_3$

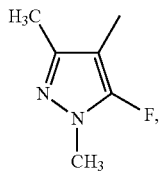

(A$_3$)

Each of Tables 7 to 9, which follow the Table X below, comprises 110 compounds of formula (Ic) in which R$_4$, R$_5$, R$_6$, R$_7$, R$_9$, R$_{10}$, R$_{11}$, R$_{12}$ and R$_{13}$ have the values given in Table X and A has the value given in the relevant Table 7 to 9. Thus Table 7 corresponds to Table X when X is 7 and A has the value given under the Table 7 heading, Table 8 corresponds to Table X when X is 8 and A has the value given under the Table 8 heading, and so on for Table 9.

TABLE X ("Me" ist the methyl group, "Et" is the ethyl group, "c-Pr" means cyclopropyl):

| Cpd No. | R$_4$ | R$_5$ | R$_6$ | R$_7$ | R$_9$ | R$_{10}$ | R$_{11}$ | R$_{12}$ | R$_{13}$ |
|---|---|---|---|---|---|---|---|---|---|
| X.001 | Me | H | H | H | H | H | H | H | H |
| X.002 | Me | H | H | H | H | H | H | Me | H |
| X.003 | Me | H | H | H | H | H | H | Et | H |
| X.004 | Me | H | H | H | H | H | H | n-Pr | H |
| X.005 | Me | H | H | H | H | H | H | c-Pr | H |
| X.006 | Me | H | H | H | H | H | H | n-Bu | H |
| X.007 | Me | H | H | H | H | H | H | i-Bu | H |
| X.008 | Me | H | H | H | H | H | H | Ph | H |
| X.009 | Me | H | H | H | Me | H | H | H | H |
| X.010 | Me | H | H | H | Et | H | H | H | H |
| X.011 | Me | H | H | H | n-Pr | H | H | H | H |
| X.012 | Me | H | H | H | c-Pr | H | H | H | H |
| X.013 | Me | H | H | H | n-Bu | H | H | H | H |
| X.014 | Me | H | H | H | Ph | H | H | H | H |
| X.015 | Me | H | H | H | OMe | H | H | H | H |
| X.016 | Me | H | H | H | Me | H | H | Me | H |
| X.017 | Me | H | H | H | Me | H | H | Et | H |
| X.018 | Me | H | H | H | Me | H | H | n-Pr | H |
| X.019 | Me | H | H | H | Me | H | H | c-Pr | H |
| X.020 | Me | H | H | H | Me | H | H | Ph | H |
| X.021 | Me | H | H | H | Et | H | H | Me | H |
| X.022 | Me | H | H | H | Et | H | H | Et | H |
| X.023 | Me | H | H | H | Et | H | H | n-Pr | H |
| X.024 | Me | H | H | H | Et | H | H | c-Pr | H |
| X.025 | Me | H | H | H | Et | H | H | Ph | H |
| X.026 | Me | H | H | H | OMe | H | H | Me | H |
| X.027 | Me | H | H | H | OMe | H | H | Et | H |
| X.028 | Me | H | H | H | OMe | H | H | n-Pr | H |
| X.029 | Me | H | H | H | OMe | H | H | c-Pr | H |
| X.030 | Me | H | H | H | OMe | H | H | Ph | H |
| X.031 | Me | H | H | H | Me | Me | H | H | H |
| X.032 | Me | H | H | H | Me | Et | H | H | H |
| X.033 | Me | H | H | H | Et | Et | H | H | H |
| X.034 | Me | H | H | H | Me | Me | H | Me | H |
| X.035 | Me | H | H | H | Me | Et | H | Me | H |
| X.036 | Me | H | H | H | Et | Et | H | Me | H |
| X.037 | Me | H | H | H | Me | Me | H | Me | H |
| X.038 | Me | H | H | H | Me | Me | H | Et | H |
| X.039 | Me | H | H | H | Me | Me | H | c-Pr | H |
| X.040 | Me | H | H | H | H | H | Me | Me | H |
| X.041 | Me | H | H | H | H | H | Et | Et | H |
| X.042 | Me | H | H | H | H | H | (CH$_2$)$_2$ | | H |
| X.043 | Me | H | H | H | H | H | (CH$_2$)$_3$ | | H |
| X.044 | Me | H | H | H | H | H | (CH$_2$)$_4$ | | H |
| X.045 | Me | H | H | H | Me | H | Me | Me | H |
| X.046 | Me | H | H | H | H | (CH$_2$) connected to R$_{12}$ | H | | H |
| X.047 | Me | H | H | H | H | (CH$_2$)$_2$ connected to R$_{12}$ | H | | H |
| X.048 | Me | Me | H | H | H | H | H | H | H |
| X.049 | Me | Me | H | H | H | H | H | Me | H |
| X.050 | Me | Me | H | H | H | H | H | Et | H |
| X.051 | Me | Me | H | H | H | H | H | n-Pr | H |
| X.052 | Me | Me | H | H | H | H | H | c-Pr | H |
| X.053 | Me | Me | H | H | H | H | H | n-Bu | H |
| X.054 | Me | Me | H | H | H | H | H | i-Bu | H |
| X.055 | Me | Me | H | H | H | H | H | Ph | H |
| X.056 | Me | Me | H | H | Me | H | H | H | H |
| X.057 | Me | Me | H | H | Et | H | H | H | H |
| X.058 | Me | Me | H | H | n-Pr | H | H | H | H |
| X.059 | Me | Me | H | H | c-Pr | H | H | H | H |
| X.060 | Me | Me | H | H | n-Bu | H | H | H | H |
| X.061 | Me | Me | H | H | Ph | H | H | H | H |
| X.062 | Me | Me | H | H | OMe | H | H | H | H |
| X.063 | Me | Me | H | H | Me | H | H | Me | H |
| X.064 | Me | Me | H | H | Me | H | H | Et | H |
| X.065 | Me | Me | H | H | Me | H | H | n-Pr | H |
| X.066 | Me | Me | H | H | Me | H | H | c-Pr | H |
| X.067 | Me | Me | H | H | Me | H | H | Ph | H |
| X.068 | Me | Me | H | H | Et | H | H | Me | H |
| X.069 | Me | Me | H | H | Et | H | H | Et | H |
| X.070 | Me | Me | H | H | Et | H | H | n-Pr | H |
| X.071 | Me | Me | H | H | Et | H | H | c-Pr | H |
| X.072 | Me | Me | H | H | Et | H | H | Ph | H |
| X.073 | Me | Me | H | H | OMe | H | H | Me | H |
| X.074 | Me | Me | H | H | OMe | H | H | Et | H |
| X.075 | Me | Me | H | H | OMe | H | H | n-Pr | H |
| X.076 | Me | Me | H | H | OMe | H | H | c-Pr | H |
| X.077 | Me | Me | H | H | OMe | H | H | Ph | H |
| X.078 | Me | Me | H | H | Me | Me | H | H | H |
| X.079 | Me | Me | H | H | Me | Et | H | H | H |
| X.080 | Me | Me | H | H | Et | Et | H | H | H |
| X.081 | Me | Me | H | H | Me | Me | H | Me | H |
| X.082 | Me | Me | H | H | Me | Et | H | Me | H |
| X.083 | Me | Me | H | H | Et | Et | H | Me | H |
| X.084 | Me | Me | H | H | Me | Me | H | Me | H |
| X.085 | Me | Me | H | H | Me | Me | H | Et | H |
| X.086 | Me | Me | H | H | Me | Me | H | c-Pr | H |
| X.087 | Me | Me | H | H | H | H | Me | Me | H |
| X.088 | Me | Me | H | H | H | H | Et | Et | H |
| X.089 | Me | Me | H | H | H | H | (CH$_2$)$_2$ | | H |
| X.090 | Me | Me | H | H | H | H | (CH$_2$)$_3$ | | H |
| X.091 | Me | Me | H | H | H | H | (CH$_2$)$_4$ | | H |
| X.092 | Me | Me | H | H | Me | H | Me | Me | H |
| X.093 | Me | Me | H | H | H | (CH$_2$) connected to R$_{12}$ | H | | H |
| X.094 | Me | Me | H | H | OMe | (CH$_2$)$_2$ connected to R$_{12}$ | H | | H |
| X.095 | Me | Me | H | H | H | H | Me | H | Me |
| X.096 | Me | Me | H | H | H | (CH$_2$)CH(CH$_3$)C(CH$_3$)$_2$ | | H | H |
| X.097 | Me | H | Me | H | H | H | H | Me | H |
| X.098 | Me | H | Me | H | Me | H | H | H | H |
| X.099 | Me | H | Me | H | Et | H | H | H | H |
| X.100 | Me | H | Me | H | Me | Me | H | Me | H |
| X.101 | Me | Me | Me | H | H | H | H | H | H |
| X.102 | Me | Me | Me | H | H | H | H | Me | H |
| X.103 | Me | Me | Me | H | Me | H | H | H | H |
| X.104 | Me | Me | Me | H | Et | H | H | H | H |
| X.105 | Me | Me | Me | H | Me | Me | H | Me | H |
| X.106 | Me | Me | H | Me | H | H | H | H | H |
| X.107 | Me | Me | H | Me | H | H | H | Me | H |
| X.108 | Me | Me | H | Me | Me | H | H | H | H |
| X.109 | Me | Me | H | Me | Et | H | H | H | H |
| X.110 | Me | Me | H | Me | Me | Me | H | Me | H |

Table 7 provides 110 compounds of formula (Id), wherein A is $A_1$

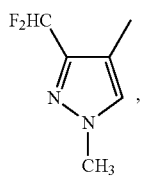

(A₁)

and $R_4$, $R_5$, $R_6$, $R_7$, $R_9$, $R_{10}$, $R_{11}$, $R_{12}$ and $R_{13}$ are as defined in Table X.

Table 8 provides 110 compounds of formula (Id), wherein A is $A_2$

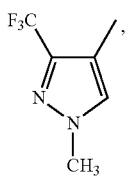

(A₂)

and $R_4$, $R_5$, $R_6$, $R_7$, $R_9$, $R_{10}$, $R_{11}$, $R_{12}$ and $R_{13}$ are as defined in Table X.

Table 9 provides 110 compounds of formula (Ic), wherein A is $A_3$

(A₃)

and $R_4$, $R_5$, $R_6$, $R_7$, $R_9$, $R_{10}$, $R_{11}$, $R_{12}$ and $R_{13}$ are as defined in Table X.

Table 10: Characterising Data:

Table 10 shows selected melting point and selected NMR data for compounds of Table 1 to 9. $CDCl_3$ is used as the solvent for NMR measurements, unless otherwise stated. If a mixture of solvents is present, this is indicated as, for example: $CDCl_3/d_6$-DMSO). No attempt is made to list all characterising data in all cases.

In Table 10 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

m.p.=melting point b.p.=boiling point.
S=singlet br=broad
d=doublet dd=doublet of doublets
t=triplet q=quartet
m=multiplet ppm=parts per million Method for GC-MS
Volatile CI/EI Mass spectra were obtained with GC-MS was conducted on a Thermo, MS: DSQ and GC: TRACE GC ULTRA with a column from Zebron phenomenex: Phase ZB-5 ms 15 m, diam: 0.25 mm, 0.25 μm, $H_2$ flow 1.7 mL/min, temp injector: 250° C., temp detector: 220° C., method: hold 2 min at 40° C., 25° C./min until 320° C., hold 1 min 12 s at 320° C., total time 15 min. All other reagents and solvents, unless otherwise noted, were purchased from commercial vendors and used without further purification.

Method for LC-MS

Method C

| | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
| LC | 1100er Series HPLC from Agilent: quaternary pump, heated column compartment and diode-array detector. Column: Waters Atlantis dc18; length: 20 mm; internal diameter: 3 mm; particle size: 3 μm, temperature (° C.) 40, DAD wavelength range (nm): 200 to 500, solvent gradient: A = 0.1% of formic acid in water and B: 0.1% of formic acid in acetonitrile. |

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

TABLE 10 phys. data for compounds of formula I:

| Cpd No. | 1H-NMR data: ppm (multiplicity/number of Hs) | MS [M + H]⁺ | m.p. (° C.) | LCMS data |
|---|---|---|---|---|
| 1.001 | | | | 2.47 (300.16) |
| 1.046 | | | | 2.60 (312.17) |
| 1.049 | | | | 3.11 (328.2) |
| 1.081 | | 356/357 | 95-105 | 3.50 (356.20) |
| 1.081 Diastereomere A | ¹H NMR (400 MHz, CHCl3-d) δ ppm 0.92 (s, 3 H), 1.10 (s, 3 H), 1.31-2.00 (m, 5 H), 1.48 (d, J = 7.0 Hz, 3 H), 1.62 (s, 3 H), 3.71 (s, 3 H), 3.98 (s, 3 H), 4.53-4.73 (m, 1 H), 4.90-5.04 (m, 1 H), 7.27 (t, J = 1.0 Hz, 1 H), 7.88 (s, 1 H) | 356/357 | solid | |
| 1.081 Diastereomere B | ¹H NMR (400 MHz, CHCl3-d) δ ppm 0.87 (s, 3 H), 1.02 (s, 3 H), 1.22-2.08 (m, 5 H), 1.32 (d, J = 7.0 Hz, 3 H), 1.61 (s, 3 H), 3.71 (s, 3 H), 3.97 (s, 3 H), 4.69-4.88 (m, 1 H), 5.01 (s, 1 H), 7.25 (t, J = 1.0 Hz, 1 H), 7.86 (s, 1 H) | 356/357 | oil | |
| 1.093 | | | | 2.95 (326.19) |
| 1.094 | | | | 2.81 (370.2) |
| 1.095 | | | | 3.32 (342.22) |
| 1.096 | | | | 4.01 (396.24) |
| 1.201 | | | | 2.53 (300.16) |
| 1.202 | | | | 2.79 (314.18) |

Formulation Examples for Compounds of Formula I

Example F-1.1 to F-1.2

Emulsifiable Concentrates

| Components | F-1.1 | F-1.2 |
|---|---|---|
| compound of Tables 1-9 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1-9 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1-9 | 80% | 10% | 5% | 95% |
| Propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1-9 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1-9 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1-9 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1-9 | 40% |
| Propylene glycol | 5% |
| copolymer butanol PO/EO | 2% |

-continued

| | |
|---|---|
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples

Example B-1

Action Against *Botrytis cinerea*—Fungal Growth Assay

Conidia of the fungus from cryogenic storage was directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition).

Compounds 1.049, 1.081, 1.081 Dia A, 1.081 Diastereomer B, 1.093, 1.094, 1.095, 1.096, and 1.202 show very good activity in this test ($\geq$80% inhibition).

Example B-2

Action Against *Mycosphaerella arachidis* (Early Leaf Spot of Groundnut; *Cercospora arachidicola* [Anamorph])—Fungal Growth Assay Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 6-7 days. The activity of a compound was expressed as fungal growth inhibition (0=no growth inhibition, ratings of 80% to 99% mean good to very good inhibition, 100%=complete inhibition).

Compounds 1.001, 1.046, 1.049, 1.081, 1.081 Diastereomer A, 1.081 Diastereomer B, 1.093, 1.094, 1.095, 1.096, 1.201 and 1.202 show very good activity in this test ($\geq$80% inhibition).

Example B-3

Action Against *Septoria tritici*—Fungal Growth Assay

Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was determined photometrically after 72 hrs. The activity of a compound was expressed as fungal growth inhibition (0=no growth inhibition, ratings of 80% to 99% mean good to very good inhibition, 100%=complete inhibition).

Compounds 1.001, 1.046, 1.049, 1.081, 1.081 Diastereomer A, 1.081 Diastereomer B, 1.093, 1.094, 1.095, 1.096, 1.201 and 1.202 show very good activity in this test ($\geq$80% inhibition).

Example B-4

Action Against *Monographella nivalis* (Anamorph: *Fusarium nivale, Microdochium nivale*; Snow Mould)—Fungal Growth Assay Conidia of the fungus from cryogenic storage were directly mixed into nutrient broth (PDB potato dextrose broth). After placing a DMSO-solution of the test compounds (0.002% active ingredient) into a microtiter plate (96-well format) the nutrient broth containing the fungal spores was added. The test plates were incubated at 24° C. and the inhibition of growth was measured photometrically after 72 hrs (0=no growth inhibition, ratings of 80% to 99% mean good to very good inhibition, 100%=complete inhibition).

Compounds 1.001, 1.046, 1.049, 1.081, 1.081 Diastereomer A, 1.081 Diastereomer B, 1.093, 1.095, 1.096, 1.201 and 1.202 show very good activity in this test ($\geq$80% inhibition).

Example B-5

Action Against Rhizoctonia Solani—Fungal Growth Assay

Mycelial fragments of a newly grown liquid culture of the fungus were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition).

Compounds 1.049, 1.081, 1.081 Diastereomer B, 1.095 and 1.096 show very good activity in this test ($\geq$80% inhibition).

Example B-6

Action Against *Erysiphe graminis* f. sp. *tritici* (Wheat Powdery Mildew)

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 7 days after inoculation as preventive fungicidal activity.

Compounds 1.049, 1.081, 1.081 Diastereomer A, 1.081 Diastereomer B, 1.093, 1.094 1.095, 1.096, and 1.202 show very good activity in this test ($\geq$80% inhibition).

Example B-7

Protective Action Against *Puccinia recondita* (Brown Rust) on Wheat

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 8 days after inoculation as preventive fungicidal activity.

Compounds 1.081, 1.081 Diastereomer A, 1.081 Diastereomer B, 1.095 and 1.096 show very good activity in this test (≧80% inhibition).

Example B-8

Curative Action Against *Puccinia recondita* (Brown Rust) on Wheat

Wheat leaf segments were placed on agar in multiwell plates (24-well format) and inoculated with a spore suspension of the fungus. One day after inoculation the leaf segments were sprayed with test solutions (0.02% active ingredient). After appropriate incubation the activity of a compound was assessed 8 days after inoculation as curative fungicidal activity.

Compounds 1.081, 1.081 Diastereomer B, 1.094 and 1.095 show very good activity in this test (≧80% inhibition).

Example B-9

Action Against *Pyrenophora teres* (Net Blotch) on Barley

Barley leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 4 days after inoculation as preventive fungicidal activity.

Compounds 1.046, 1.049, 1.081, 1.081 Diastereomer A, 1.081 Diastereomer B, 1.093, 1.094, 1.095, 1.096 and 1.202 show very good activity in this test (≧80% inhibition).

What is claimed is:

1. A compound of formula I

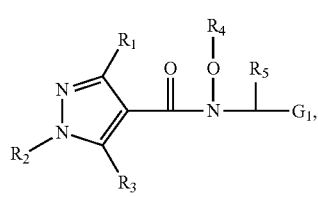

(I)

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl;
$G_1$ is a cyclohexenyl group which is mono- or polysubstituted by substituents selected from the group consisting of $C_1$-$C_6$alkyl, $C_1$-$C_6$alkoxy, $C_3$-$C_6$cycloalkyl and phenyl; said cyclohexenyl group can form together with a $C_1$-$C_4$alkylene group a bicyclic system which can be mono- or polysubstituted by substituents selected from the group consisting of $C_1$-$C_6$alkyl, $C_1$-$C_6$alkoxy, $C_3$-$C_6$cycloalkyl and phenyl;
and agronomically acceptable salts/stereoisomers/diastereoisomers/enantiomers/tautomers and N-oxides of those compounds.

2. A compound of formula I represented by the compounds of formula Ia

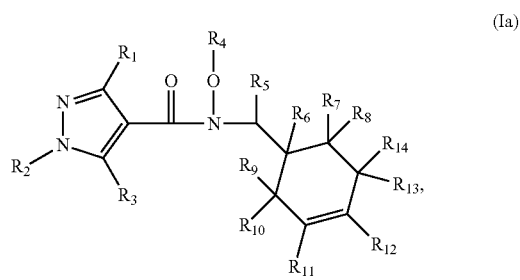

(Ia)

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl;
$R_6$, $R_7$, $R_8$, $R_9$, $R_{10}$, $R_{11}$, $R_{12}$, $R_{13}$ and $R_{14}$, independently from each other, are hydrogen, $C_1$-$C_6$alkyl, $C_1$-$C_6$alkoxy, $C_3$-$C_6$cycloalkyl or phenyl; or $R_{10}$ and $R_{13}$ together or $R_9$ and
$R_{14}$ together form a methylene or ethylene bridge which can be mono- or disubstituted by $C_1$-$C_4$alkyl.

3. A compound of formula Ia according to claim 2, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$ is hydrogen or $C_1$-$C_4$alkyl;
$R_6$ is hydrogen;
$R_7$ is hydrogen;
$R_8$ is hydrogen;
$R_9$ is hydrogen, $C_1$-$C_4$alkyl or $C_1$-$C_4$alkoxy;
$R_{10}$ is hydrogen or $C_1$-$C_4$alkyl;
$R_{11}$ is hydrogen or $C_1$-$C_4$alkyl;
$R_{12}$ is hydrogen or $C_1$-$C_4$alkyl;
$R_{13}$ is hydrogen or $C_1$-$C_4$alkyl;
$R_{14}$ is hydrogen;
or $R_{10}$ and $R_{13}$ together form a methylene or ethylene bridge which can be mono- or disubstituted by $C_1$-$C_4$alkyl.

4. A compound of formula Ia according to claim 3, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$ is $C_1$-$C_4$alkyl;
$R_6$, $R_7$ and $R_8$ are hydrogen;
$R_9$ is $C_1$-$C_4$alkyl;
$R_{10}$ is $C_1$-$C_4$alkyl;
$R_{11}$ is hydrogen;
$R_{12}$ is $C_1$-$C_4$alkyl; and
$R_{13}$ and $R_{14}$ are hydrogen.

5. A compound of formula I according to claim 1 represented by the compounds of formula Ie

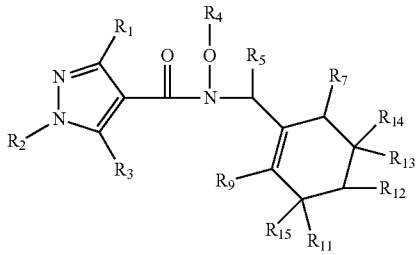
(Ie)

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$haloalkyl;
$R_5$ is hydrogen, halogen, $C_1$-$C_4$alkyl or $C_1$-$C_4$haloalkyl;
$R_7$, $R_9$, $R_{11}$, $R_{12}$, $R_{13}$ and $R_{14}$ and $R_{15}$ independently from each other, are hydrogen, $C_1$-$C_6$alkyl, $C_1$-$C_6$alkoxy, $C_3$-$C_6$cycloalkyl or phenyl;
and $R_{12}$ is hydrogen or $C_1$-$C_4$alkyl; or $R_{11}$ and $R_{14}$ together or $R_{15}$ and $R_{13}$ together form a methylene or ethylene bridge which can be mono- or disubstituted by $C_1$-$C_4$alkyl.

6. A compound of formula Ie according to claim 5, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$, $R_7$, $R_9$, $R_{11}$, $R_{13}$ and $R_{14}$ and $R_{15}$ are hydrogen and $R_{12}$ is hydrogen or $C_1$-$C_4$alkyl.

7. A compound of formula I according to claim 1, wherein $R_4$ is methyl.

8. A compound of formula I according to claim 1, wherein $R_5$ is methyl.

9. A method of controlling or preventing infestation of useful plants by phytopathogenic microorganisms, wherein a compound of formula I according to claim 1 or a composition, comprising this compound as active ingredient, is applied to the plants, to parts thereof or the locus thereof.

10. A composition for controlling and protecting against phytopathogenic microorganisms, comprising a compound of formula I according to claim 1 and at least one auxiliary.

* * * * *